United States Patent
Cindrich et al.

(10) Patent No.: US 12,376,862 B2
(45) Date of Patent: Aug. 5, 2025

(54) COVERED VASCULAR PLUG

(71) Applicant: Merit Medical Systems, Inc., South Jordan, UT (US)

(72) Inventors: Christopher Cindrich, Highland, UT (US); John Hall, Bountiful, UT (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 247 days.

(21) Appl. No.: 17/816,142

(22) Filed: Jul. 29, 2022

(65) Prior Publication Data
US 2023/0030299 A1 Feb. 2, 2023

Related U.S. Application Data

(60) Provisional application No. 63/228,326, filed on Aug. 2, 2021.

(51) Int. Cl.
*A61B 17/12* (2006.01)
*A61L 24/06* (2006.01)

(52) U.S. Cl.
CPC .. *A61B 17/12145* (2013.01); *A61B 17/12031* (2013.01); *A61B 17/12109* (2013.01); *A61L 24/06* (2013.01); *A61B 2017/12095* (2013.01)

(58) Field of Classification Search
CPC .......... A61B 17/1215; A61B 17/12145; A61B 17/12168; A61B 17/12172; A61B 17/12177; A61B 17/12027; A61B 17/12031; A61B 17/12099; A61B 17/12109; A61B 17/12131; A61B 2017/12095

See application file for complete search history.

(56) References Cited

U.S. PATENT DOCUMENTS

| | | | |
|---|---|---|---|
| 2004/0181253 A1 | 9/2004 | Sepetka et al. | |
| 2007/0265656 A1 | 11/2007 | Amplatz et al. | |
| 2014/0215792 A1 | 8/2014 | Leopold et al. | |
| 2014/0257361 A1* | 9/2014 | Prom | A61B 17/12172 606/198 |
| 2015/0157333 A1* | 6/2015 | Leopold | A61B 17/12145 29/428 |

(Continued)

FOREIGN PATENT DOCUMENTS

| | | |
|---|---|---|
| WO | 2013159065 A1 | 10/2013 |
| WO | 2018058033 A1 | 3/2018 |

(Continued)

OTHER PUBLICATIONS

International Search Report and Written Opinion dated Nov. 17, 2022 for PCT/US2022/074324.
European Search Report dated May 7, 2025 for EP22854031.6.

*Primary Examiner* — Tuan V Nguyen
(74) *Attorney, Agent, or Firm* — Dorsey & Whitney LLP

(57) ABSTRACT

Devices used to restrict flow within a blood vessel are disclosed. Devices within the scope of this disclosure include a braided lattice of nitinol wires that form self-expanding enclosures of an embolic structure. The devices may further include embolic particles disposed within the enclosures. Methods of deploying the devices with the embolic particles are disclosed. Methods of manufacturing the devices with the embolic particles disposed within the enclosures are disclosed.

17 Claims, 8 Drawing Sheets

(56) References Cited

U.S. PATENT DOCUMENTS

| | | | |
|---|---|---|---|
| 2016/0101271 A1* | 4/2016 | Rudakov | A61N 5/1002 |
| | | | 604/20 |
| 2016/0151056 A1 | 6/2016 | Lederman et al. | |
| 2017/0035437 A1* | 2/2017 | Sarge | A61B 17/12163 |
| 2017/0296198 A1* | 10/2017 | Rudakov | A61B 17/12036 |
| 2018/0235639 A1* | 8/2018 | DeMeritt | A61B 17/12031 |
| 2020/0261098 A1 | 8/2020 | Lubock et al. | |
| 2021/0267605 A1* | 9/2021 | Rudakov | A61B 17/12109 |

FOREIGN PATENT DOCUMENTS

| | | | |
|---|---|---|---|
| WO | 2020243039 A1 | 12/2020 | |
| WO | 2021120625 A1 | 6/2021 | |
| WO | 2021226014 A2 | 11/2021 | |

* cited by examiner

COVERED VASCULAR PLUG

RELATED APPLICATIONS

This application claims priority to U.S. Provisional Application No. 63/228,326, filed on Aug. 2, 2021 and titled, "Covered Vascular Plug," which is hereby incorporated by reference in its entirety.

TECHNICAL FIELD

The present disclosure generally relates to intravascular devices for treating certain medical conditions, including use of low-profile intravascular occlusion devices for treating vascular defects and/or to prevent blood flow within a vessel.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
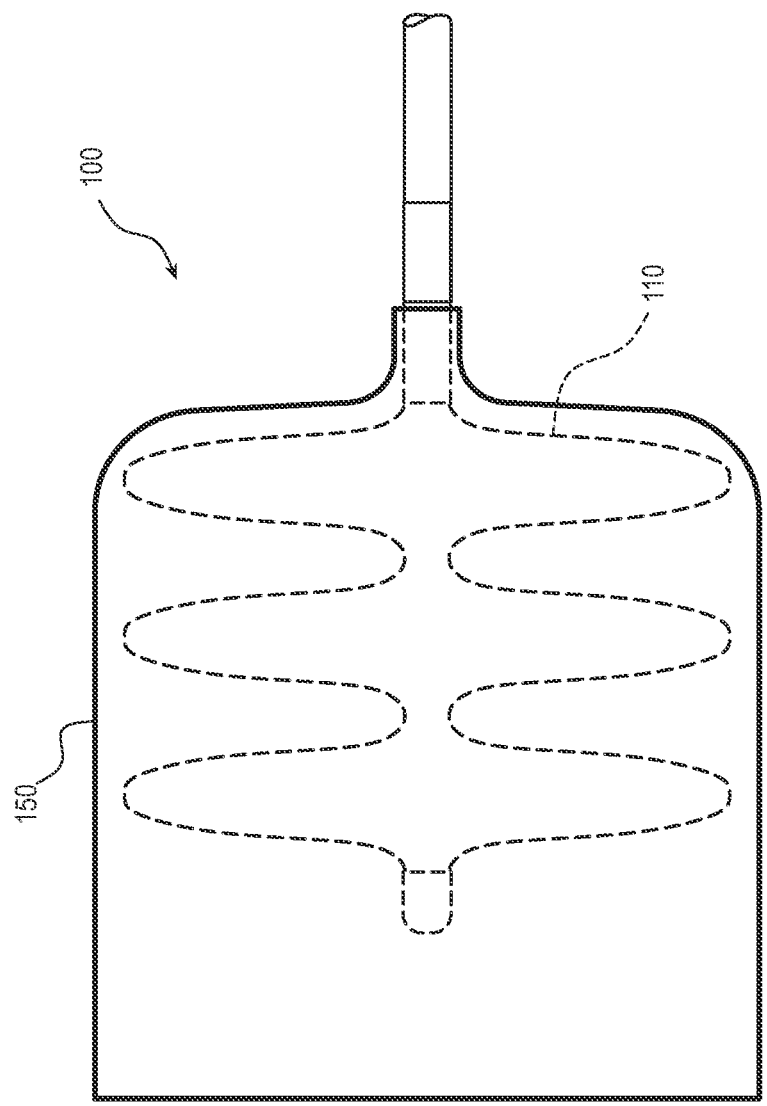
FIG. 1 is a side view of an embodiment of an embolization device in an expanded state with an embolic member disposed over an embolic structure.

Intravascular devices are used in various medical procedures. For example, embolization devices may be used to treat arterial-venous malformations, aneurysms, and other vascular defects, or to prevent blood flow to tumors or other portions of the body.

In some instances, an embolization device includes an embolic structure comprising a plurality of enclosures or baskets. Enclosures within the scope of this disclosure include baskets of a woven lattice or matrix, including embodiments formed of nitinol wires. The plurality of enclosures may be coupled together and may be releasably coupled to a placement wire. The enclosures can be crimped or constrained to a small diameter and disposed within a delivery catheter for deployment into a body lumen such as a blood vessel. In some embodiments, in a fully expanded configuration, the enclosures have a disk shape or a partial disk-like shape with opposing sides disposed in a generally parallel arrangement. In a partially expanded state, the enclosures may be elongate, spherical, ovoid, cylindrical, or other shapes. The enclosures may be configured to restrict blood flow through the blood vessel when deployed within a blood vessel. When deployed the enclosure may be fully or partially expanded, including instances where the degree of expansion is controlled by interaction between the vessel wall and the enclosure.

In some embodiments within the scope of this disclosure, an embolic member may be disposed over or between one or more enclosures and deployed with the enclosures. When deployed, the embolic member may increase the restriction of blood flow through the blood vessel. Stated another way, a plurality of enclosures wherein the embolic member is disposed over or between one or more enclosures may reduce flow through a vessel more than the plurality of enclosures alone. In certain embodiments, the embolic member is a polymeric sleeve disposed over at least one enclosure such that the at least one enclosure is free-floating within the sleeve. In another embodiment, the embolic member is a polymeric disk disposed between two adjacent enclosures.

Embolization devices within the scope of this disclosure can be manufactured by weaving filaments to create a lattice or basket defining the enclosure. Filaments within the scope of this disclosure include metals and polymers, including superelastic or shape memory materials. For example, nitinol wires may be used to form the embolic structure of the enclosures. In some embodiments, a continuous weave of filaments may be used to form a plurality of enclosures with necked down middle portions disposed between the enclosures. During manufacturing, the embolic member can be disposed over or between the enclosures, with the enclosures in a crimped state. The embolic structure, with the embolic member, may be crimped to a small diameter to fit within a delivery catheter.

An embolization device may be used in procedures to occlude vascular structures such as blood vessels. The embolization device can be deployed into a blood vessel by positioning a guide catheter at a desired deployment location for the embolization device, inserting the delivery catheter into the guide catheter, deploying the embolic structure with the embolic member disposed over or between the enclosures of the embolic structure into the blood vessel, and releasing the embolic structure from a placement wire. Once deployed, the embolic structure can self-expand until it contacts the vessel wall. When expanded, the woven lattice of the embolic structure and the embolic member may restrict blood flow through the blood vessel. In certain instances, the restricted blood flow through the blood vessel results in formation of a thrombus or clot within the blood vessel.

Embodiments may be understood by reference to the drawings. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings or figures, these are not necessarily drawn to scale unless specifically indicated.

Various features are sometimes grouped together in a single embodiment, figure, or description thereof for the purpose of streamlining the disclosure. Many of these features may be used alone and/or in combination with one another.

Figure 2:
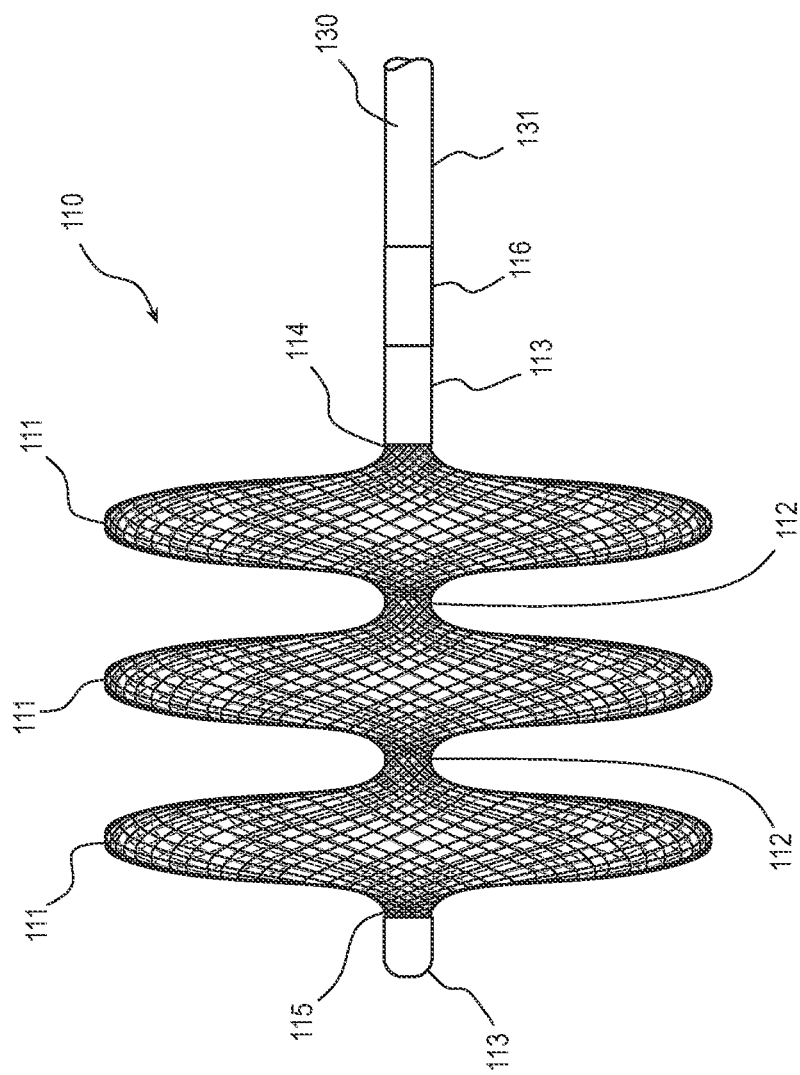
FIG. 2 is a side view of the embolic structure of the embolization device of FIG. 1 in the expanded state.
Figure 3A:
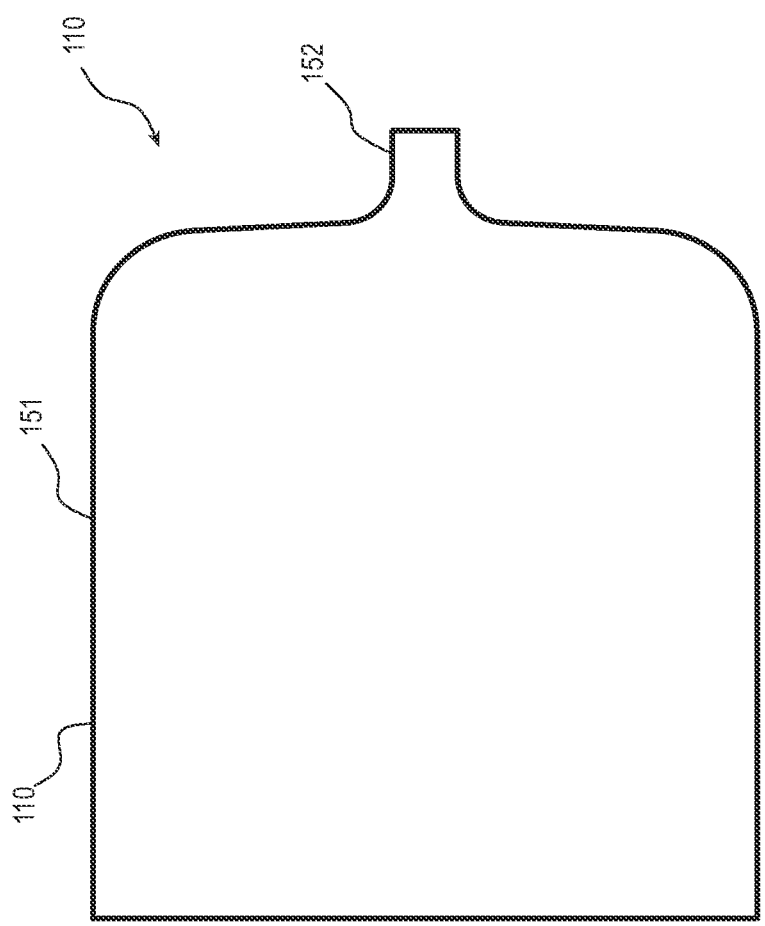
FIG. 3A is a side view of the embolic member of the embolization device of FIG. 1.
Figure 3B:
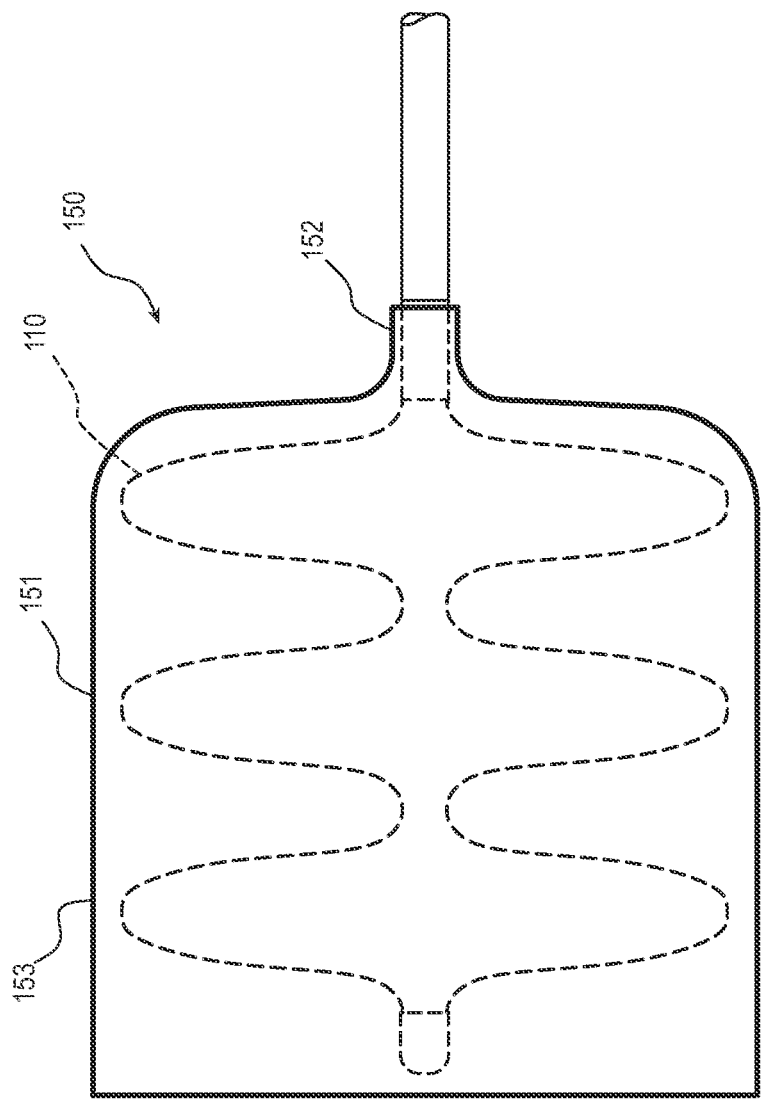
FIG. 3B is a side view of the embolic member of the embolization device of FIG. 1 with the embolic member in a partially expanded state.
Figure 4A:
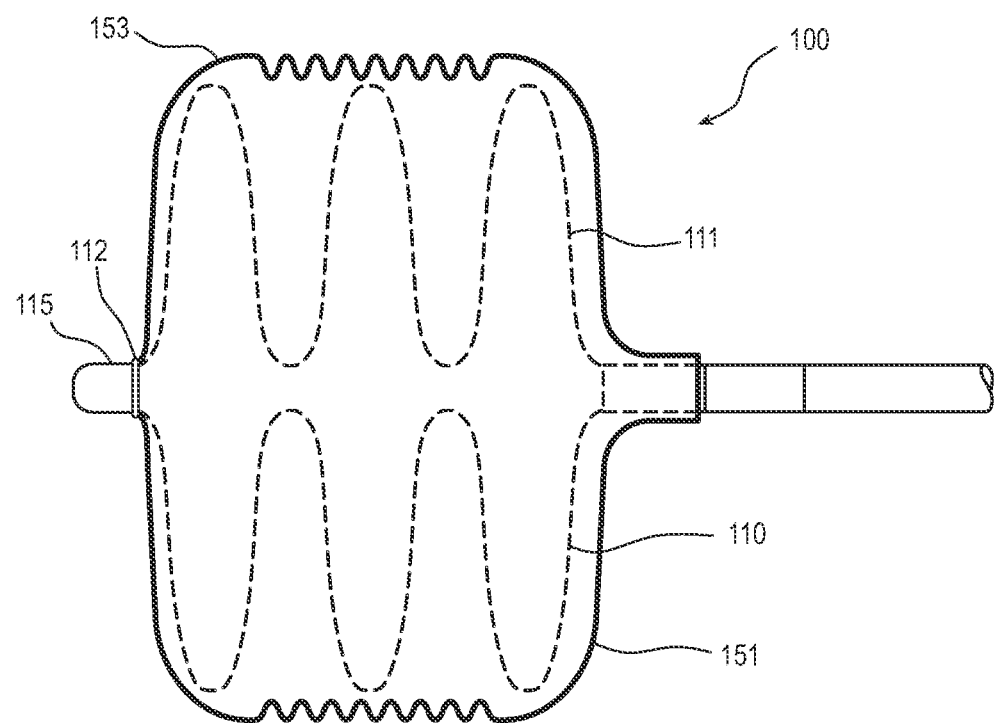
FIG. 4A is a side view of another embodiment of an embolization device in an expanded state with an embolic member disposed over an embolic structure.
Figure 4B:
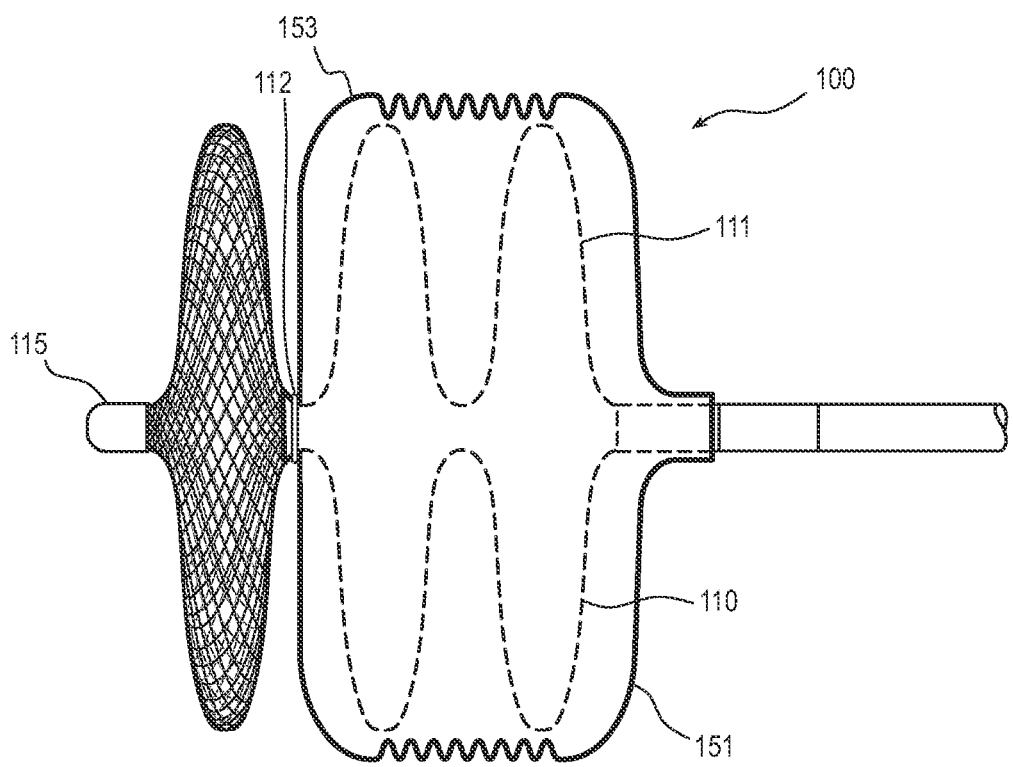
FIG. 4B is a side view of another embodiment of an embolization device in an expanded state with an embolic member partially disposed over an embolic structure.
Figure 5:
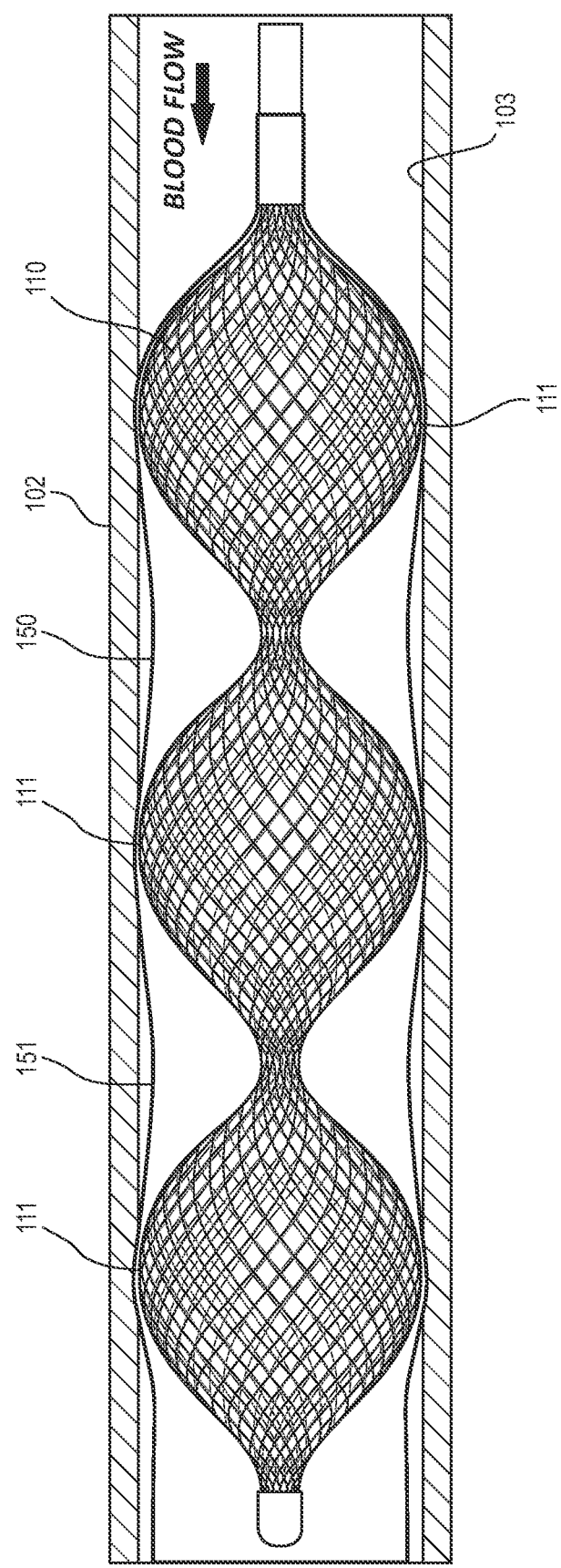
FIG. 5 is a partial cross-sectional view of the embolization device of FIG. 1 partially expanded and disposed within a vessel.
Figure 6:
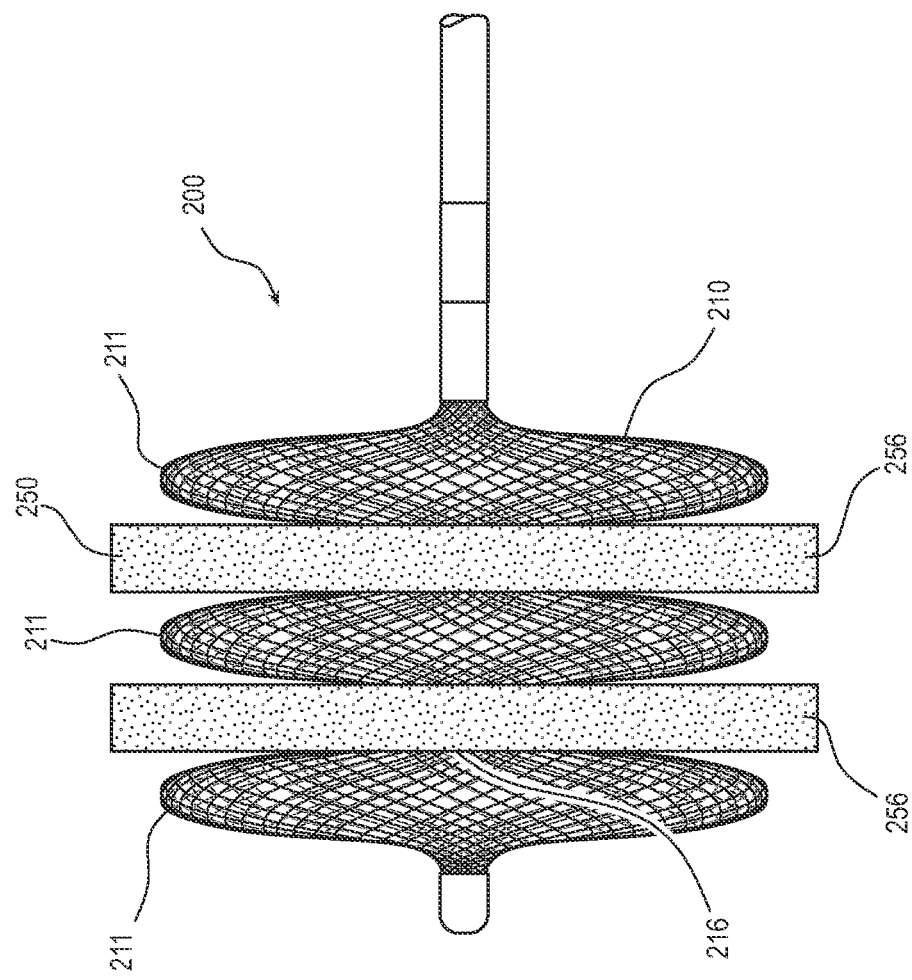
FIG. 6 is a side view of another embodiment of an embolization device in an expanded state with an embolic member disposed between adjacent enclosures of an embolic structure.
Figure 7:
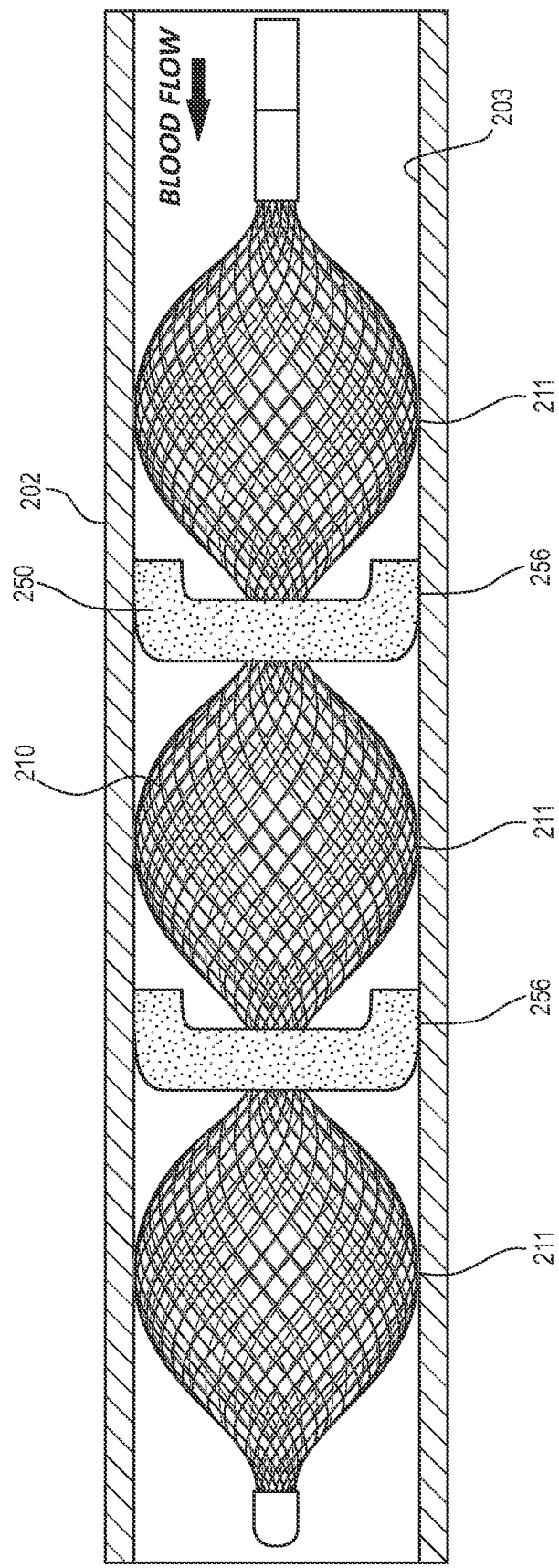
FIG. 7 is a side view of the embolization device of FIG. 6 in a partially expanded state and disposed within a vessel.

FIGS. 1-7 illustrate different views of embolic devices and related components. FIG. 1 is a side view of an embodiment of an embolization device in an expanded state with an embolic member disposed over an embolic structure. FIG. 2 is a side view of the embolic structure of the embolization device of FIG. 1 in the expanded state. FIG. 3A is a side view of the embolic member of the embolization device of FIG. 1. FIG. 3B is a side view of the embolic member of the embolization device of FIG. 1 with the embolic member in a partially expanded state. FIG. 4A is side view of another embodiment of an embolization device in an expanded state with an embolic member disposed over an embolic structure. FIG. 4B is a side view of another embodiment of an embolization device in an expanded state with an embolic member partially disposed over an embolic structure. FIG. 5 is a partial cross-sectional view of the embolization device of FIG. 1 partially expanded and disposed within a vessel. FIG. 6 is a side view of another embodiment of an embolization device in an expanded state with an embolic member disposed between adjacent enclosures of an embolic structure. FIG. 7 is a side view of the embolization device of FIG. 6 in a partially expanded state and disposed within a vessel. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 depicts one embodiment of an embolization device 100 in a pre-load or expanded state. In the illustrated embodiment, the embolization device 100 includes an embolic structure 110 and an embolic member 150 disposed over the embolic structure 110 and configured to be a physical barrier to blood flow through a vessel. The embolic structure 110 may be free-floating within the embolic member 150, allowing the embolic structure 110 to lengthen within the embolic member 150 when the embolic structure 110 is radially compressed.

FIG. 2 illustrates the embolic structure 110. As illustrated, the embolic structure 110 is composed of three enclosures or baskets 111 with necked down portions 112 disposed between the enclosures 111. In another embodiment, the embolic structure 110 may include a single enclosure 111. In yet another embodiment, the embolic structure 110 may include two enclosures 111 with a necked down portion 112 disposed between the two enclosures 111. Embodiments with more than three enclosures 111, including embodiments with four, five, six, or more enclosures 111, are likewise within the scope of this disclosure. In the illustrated embodiment, in the pre-load or expanded state, the enclosures 111 have a disk shape. Embodiments where the expanded shape is spherical, ovoid, cylindrical, or any other shape are likewise within the scope of this disclosure. In certain embodiments, the enclosures 111 of the embolic structure 110 may be all the same size and shape or may be of different sizes and shapes. For example, a proximal enclosure may be cylindrical in shape and approximately two millimeters in diameter and a distal enclosure may be circular in shape and approximately 1.5 millimeters in diameter. In a further example, a proximal enclosure may be cylindrical and a subsequent distal enclosure may be ovoid. In some embodiments, when the enclosures 111 number two or more and the shapes are not symmetrical about the placement wire 130, the enclosures 111 may be aligned or misaligned one to another.

In the illustrated embodiment, the embolic structure 110 includes a woven lattice or matrix of woven nitinol wires. The ends of the wires can be restrained by clamps 113 disposed at a proximal end 114 and a distal end 115 to prevent fraying of the braid. The embolic structure 110 can be releasably coupled to a placement wire 130 for deployment. For example, in the illustrated embodiment the embolic structure 110 includes a threaded coupling 116 disposed at the proximal end 114 that can be threadingly coupled to a threaded end 131 of the placement wire 130. When deployed the embolic structure 110 can be rotationally held in place relative to the placement wire 130 when the embolic structure 110 engages with the vessel wall and the placement wire 130 can be rotated to release the placement wire 130 from the embolic structure 110. Other mechanisms for release and deployment are also within the scope of this disclosure including, hooks, collets, loops, snares, and so forth.

FIG. 3A depicts the embolic member 150. In the depicted embodiment, the embolic member 150 includes a hollow, cylindrical sleeve 151 having an open proximal end 152 and an open distal end 153. A diameter of the proximal end 152 is substantially equivalent to a diameter of the proximal end 114 of the embolic structure such that the proximal end 152 is sized to fit over the proximal end 114 and too small to fit over the enclosures 111 of the embolic structure 110 when the enclosures 111 are at least partially expanded. The diameter of the proximal end 152 can range from about 50% smaller than a diameter of the placement wire 130 to about 50% larger than the diameter of the placement wire 130. This embodiment of the embolic structure 110 can prevent the proximal end 152 of the sleeve 151 from being displaced distally over the enclosures 111 by blood flow when the embolization device 100 is deployed within the vessel. In another embodiment, the proximal end 152 of the sleeve 151 can be fixedly coupled to the proximal end 114 of the embolic structure 110 using any suitable technique, such as clamping, banding, bonding, welding, filament, etc. Other coupling techniques are contemplated.

A diameter of the distal end 153 of the sleeve 151 is substantially equivalent to a diameter of the enclosures 111 when the enclosures 111 are fully expanded. This configuration allows the embolic structure 110 to be free-floating within the sleeve 151. When the enclosures 111 are in the partially expanded state, a length of the embolic structure 110 can be longer than a length of the embolic structure 110 when the enclosures 111 are in the fully expanded state. As illustrated in the embodiment of FIG. 3B, the sleeve 151 can be sized in length to extend distally beyond the distal end 115 of the embolic structure 110 when the enclosures are at least partially expanded. In other words, the sleeve 151 may be configured to cover the enclosures 111 whether in the fully expanded state or in the partially expanded state. The diameter of the distal end 153 of the sleeve 151 may allow the embolic structure 110 to lengthen without restriction as the enclosures 111 transition from the fully expanded state to the partially expanded state because the embolic structure 110 is free-floating within the sleeve 151. Additionally, the diameter of the distal end 153 may allow the embolic structure 110 to shorten as the enclosures 111 transition from the partially expanded state to the fully expanded state because the embolic structure 110 is free-floating within the sleeve 151.

In other embodiments, the sleeve 151 may be sized in length to extend distally beyond only a proximal enclosure 111. Other lengths of the sleeve 151 are considered within the scope of this disclosure.

In an alternative embodiment illustrated in FIG. 4A, the distal end 153 of the sleeve 151 is radially gathered and fixedly coupled to the distal end 115 of the embolic structure 110. In such embodiments, the distal end 153 of the sleeve 151 may be longitudinally compressed or crinkled when the enclosures 111 are in the fully expanded state, as depicted in FIG. 4A, and configured to longitudinally elongate when the enclosures 111 transition to the partially expanded state. The distal end 115 may be elongated when the enclosures 111 are in the partially expanded state and configured to longitudinally compress or crinkle when the enclosures 111 transition from the partially expanded state to the fully expanded state. The distal end 153 of the sleeve 151 can be coupled to the distal end 115 of the embolic structure 110 using any suitable technique, such as clamping, banding, bonding, welding, filament, etc. Other coupling techniques are contemplated.

In another alternative embodiment illustrated in FIG. 4B, the distal end 153 of the sleeve 151 is radially gathered and fixedly coupled to a necked down portion 112 of the embolic structure 110. In such embodiments, the sleeve 151 may be longitudinally compressed or crinkled when the enclosures 111 are in the fully expanded state, as shown in FIG. 4B, and configured to longitudinally elongate when the enclosures 111 transition to the partially expanded state. The distal end 115 may be elongated when the enclosures 111 are in the partially expanded state and configured to longitudinally compress or crinkle when the enclosures 111 transition from the partially expanded state to the fully expanded state. The distal end 153 of the sleeve 151 can be coupled to the necked down middle portion of the embolic structure 110 using any suitable technique, such as clamping, bonding, banding, welding, filament, etc. Other coupling techniques are contemplated.

In some embodiments, the embolic member 150 can include a polymeric, conformable mat. In certain embodiments, the mat may be non-porous or have pores sized to prevent or restrict blood flow through the embolic member 150. The mat may be formed by serially depositing micro or nano fibers on a mandrel using any suitable technique. For example, in one embodiment, the micro or nano fibers are serially deposited using a rotational spinning technique where a polymer solution is expelled from a dispenser using centrifugal force. In another embodiment, the micro or nano fibers are serially deposited using an electro spinning technique where a polymer solution is expelled from an orifice having an electrical charge toward a surface having an opposite electrical charge. The polymer of the polymer solution can be polytetrafluoroethylene (PTFE).

In certain embodiments, the embolic member 150 includes expanded polytetrafluoroethylene (ePTFE). In other embodiments, the embolic member 150 includes any other suitable material capable of preventing blood flow through the embolic member 150, such as silicone, fluorinated ethylene propylene (FEP), etc. Embodiments wherein the embolic member 150 is formed of natural materials, synthetic materials, porous materials, bioabsorbable materials, biostable material, and other materials are all within the scope of this disclosure. In some embodiments, the embolic member 150 may include a thrombogenic agent configured to promote thrombus formation adjacent the embolic member 150.

In certain embodiments, the embolic structure 110 and the embolic member 150 may be provided to a user in the expanded state such as shown in FIG. 1. When preparing the embolic structure 110 for use, the user may transition the embolic structure 110 and the embolic member 150 into a constrained state by pulling or otherwise disposing the embolic structure 110 and the embolic member 150 into a delivery catheter to reduce a diameter of the embolic structure 110 and the embolic member 150.

In another embodiment, the embolic structure 110 and the embolic member 150 may be provided to a user in the constrained state where the embolic structure 110 and the embolic member 150 are crimped to a small diameter and disposed within the delivery catheter.

The embolization device 100 can be deployed within a blood vessel by advancing the delivery catheter containing the embolic structure 110 and the embolic member 150 to a treatment location in the body and deploying the embolic structure 110 and the embolic member 150. In some embodiments, this may include loading the delivery catheter containing the constrained embolic structure 110 and the embolic member 150 into a guide catheter and advancing the delivery catheter to a distal end of the guide catheter. The delivery catheter may be displaced proximally relative to the embolic structure 110 and the embolic member 150 such that the embolic structure 110 and the embolic member 150 are disposed within the blood vessel. The embolic structure 110 may be configured to self-expand as it is deployed within the blood vessel.

During such deployments, the embolic structure 110 and the embolic member 150 may be disposed within the blood vessel simultaneously such that a secondary deployment is not needed. That is, placing an embolic structure including enclosures and an embolic member within a blood vessel may simultaneously place the enclosures and the embolic member within the blood vessel. Similarly, a single deployment action, such as retracting a delivery catheter, may thus deliver both the enclosures and the embolic member into the blood vessel in a deployed configuration.

When deployed within a blood vessel 102, the embolic structure 110 and the embolic member 150 can transition from the constrained state to the partially expanded state, such as shown in FIG. 5. In some embodiments, the enclosures 111 may self-expand when disposed outside the delivery catheter until the enclosures 111 contact a vessel wall 103. The placement wire 130 may be decoupled from the embolic structure 110, for example by rotating the placement wire relative to the embolic structure 110 to release the placement wire 130 from the embolic structure 110. As shown, the enclosures 111 of the embolic structure 110 are partially radially expanded and the embolic member 150 is disposed between the enclosures 111 and the vessel wall 103.

When deployed, the embolic structure 110 and the embolic member 150 can form a physical blood flow restrictor within the blood vessel 102. Embolic member 150 thickness, pore size, density of filaments in the enclosures 111, degree of expansion of the enclosures 111, and other parameters may affect the degree to which flow across the device is restricted. Embodiments wherein blood flow is reduced from about 10% to about 50% or more are within the scope of this disclosure.

FIGS. 6 and 7 depict an embodiment of an embolization device 200 that resembles the embolization device 100 described above in certain respects. Accordingly, like features are designated with like reference numerals, with the leading digit incremented to "2." For example, the embodiment depicted in FIGS. 6 and 7 includes an embolic structure 210 that may, in some respects, resemble the embolic structure 110 of FIG. 2. Relevant disclosure set forth above regarding similarly identified features thus may not be repeated hereafter. Moreover, specific features of the embolization device 100 and related components shown in FIGS. 1-5 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the embolization device 200 and related components depicted in FIGS. 6 and 7. Any suitable combination of the features, and variations of the same, described with respect to the embolization device 100 and related components illustrated in FIGS. 1-5 can be employed with the embolization device 200 and related components of FIGS. 6 and 7, and vice versa.

FIG. 6 illustrates another embodiment of an embolization device 200. As illustrated, the embolization device 200 includes an embolic structure 210 similar to the embolic structure 110 previously discussed and an embolic member 250. The embolic member 250 can be an embolic disk 256 having a circular shape. In other embodiments, the embolic disk 256 can be of any suitable shape. For example, the shape of the embolic disk 256 can be triangular, square, pentagonal, hexagonal, etc. Other disk shapes are contemplated. A thickness of the embolic disk 256 may range from about 0.0254 millimeter to about 0.508 millimeter. A diameter of the embolic disk 256 may range from about 10% to about 200% of a diameter of the enclosure 211. In some embodiments, the diameter of the embolic disk 256 may be about equivalent to or slightly larger than a diameter of an enclosure 211 when in the fully expanded state.

The embolic disk 256 can be disposed at a necked down portion 212 between adjacent enclosures 211 such that the embolic disk 256 surrounds the necked down portion 112 of the embolic structure 210. As depicted in FIG. 6, the embolic disks 256 can be disposed at a plurality of locations along the embolic structure 210. In another embodiment, a single embolic disk 256 can be disposed anywhere along a length of the embolic structure 210 between any two adjacent enclosures 211. In still another embodiment, the embolic structure 210 may include a single enclosure 211 and a single embolic disk 256 disposed proximal of the single enclosure 211 to prevent the single embolic disk 256 from being displaced distally by blood flow. As illustrated in FIG. 6, a single embolic disk 256 is disposed between adjacent enclosures 211. In some embodiments, two, three, or more embolic disks 256 may be disclosed between adjacent enclosures 211.

The embolic disk 256 can include a center through hole such that the embolic disk 256 may be slid over the enclosures 211 from either end of the embolic structure 210 when the enclosures 211 are in a partially expanded or crimped state. In another embodiment, the embolic disk 256 can include a slit disposed through the embolic disk 256 and extending from a circumference to a central point or the through hole of the embolic disk 256. In certain embodiments, the embolic disk 256 may be coupled to the embolic structure 210 using any technique, such as bonding, gluing, welding, etc.

FIG. 7 illustrates the embolic structure 210 and the embolic disk 252 deployed in a blood vessel 202. When deployed within the blood vessel 202, the embolic structure 210 and the embolic member 250 can transition from a crimped state to a partially expanded state, such as shown in FIG. 7. In some embodiments, the enclosures 211 may self-expand when disposed outside a delivery catheter until the enclosures 211 contact a vessel wall 203. As shown, the enclosures 211 of the embolic structure 210 are partially radially expanded and the embolic disks 256 are also partially radially expanded such that they contact the vessel wall 203.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of restricting blood flow within a blood vessel, comprising: positioning an embolization device into the blood vessel adjacent to a treatment site; deploying the embolization device from a delivery catheter into the blood vessel at the treatment site; self-expanding an enclosure of an embolic structure of the embolization device within the blood vessel wherein the enclosure contacts a wall of the blood vessel; expanding an embolic member coupled to the embolic structure; and restricting blood flow through the embolic member.

References to approximations are made throughout this specification, such as by use of the term "about." For each such reference, it is to be understood that, in some embodiments, the value, feature, or characteristic may be specified without approximation. For example, where a qualifier such as "about" is used, this term includes within its scope the qualified words in the absence of its qualifiers. For example, where the term "about" is recited with respect to a feature, it is understood that in further embodiments, the feature can have a precise configuration.

The phrase "coupled to" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use.

The terms "a" and "an" can be described as one, but not limited to one. For example, although the disclosure may recite a housing having "a stopper," the disclosure also contemplates that the housing can have two or more stoppers.

Unless otherwise stated, all ranges include both endpoints and all numbers between the endpoints.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. An embolization device, comprising:
   an embolic structure comprising a plurality of self-expanding enclosures, wherein each of the plurality of self-expanding enclosures comprise a braided lattice of nitinol wires; and
   an embolic member comprising a sleeve disposed adjacent at least one of the plurality of self-expanding enclosures;
   wherein a distal end of the sleeve is disposed proximal to a distal end of the embolic structure.

2. The embolization device of claim 1, wherein the embolic member is formed of any one of polytetrafluoroethylene (PTFE), silicone, polyester, fluorinated ethylene propylene (FEP), graphene, and any combination thereof.

3. The embolization device of claim 2, wherein the PTFE is any one of rotational spun PTFE, electrospun PTFE, expanded PTFE, and any combination thereof.

4. The embolization device of claim 1, wherein the sleeve is configured to be disposed over the embolic structure.

5. The embolization device of claim 4, wherein the embolic structure is free-floating within the sleeve.

6. The embolization device of claim 4, wherein the sleeve comprises a proximal portion having a first diameter sized to receive a proximal end of the embolic structure and a distal portion having a second diameter sized to receive at least one of the plurality of self-expanding closures.

7. The embolization device of claim 6, wherein the first diameter is smaller than a diameter of at least one of the plurality of self-expanding enclosures.

8. The embolization device of claim 6, wherein the second diameter is larger than a diameter of each one of the plurality of self-expanding enclosures.

9. The embolization device of claim 6, wherein the distal portion of the sleeve is fixedly coupled to the embolic structure between any adjacent enclosures of the plurality of enclosures.

10. The embolization device of claim 6, wherein the proximal portion of the sleeve is fixedly coupled to the proximal end of the embolic structure.

11. The embolization device of claim 1, wherein one of the plurality of self-expanding enclosures includes a diameter different than a diameter of an adjacent self-expanding enclosure of the plurality of self-expanding enclosures.

12. An intravascular occlusion system, comprising:
   an embolization device comprising:
      an embolic structure comprising a plurality of self-expanding enclosures, wherein each of the plurality of self-expanding enclosures comprise a braided lattice of nitinol wires; and
      an embolic member comprising a sleeve configured to be disposed over the embolic structure and disposed adjacent at least one of the plurality of self-expanding enclosures, wherein a distal end of the sleeve is disposed proximal to a distal end of the embolic structure; and
   a delivery wire selectively coupled to the embolic structure.

13. The intravascular occlusion system of claim 12, wherein the delivery wire comprises a threaded distal end, wherein the embolic structure comprises a threaded coupling disposed at a proximal end, and wherein the delivery wire is configured to be rotationally disengaged from the embolic structure.

14. The intravascular occlusion system of claim 12, wherein the sleeve is disposed over at least one enclosure of the plurality of enclosures.

15. A method of restricting blood flow within a blood vessel, comprising:
   positioning an embolization device into the blood vessel adjacent to a treatment site;
   deploying the embolization device from a delivery catheter into the blood vessel at the treatment site;
   self-expanding an enclosure of an embolic structure of the embolization device within the blood vessel wherein the enclosure contacts a wall of the blood vessel;
   expanding an embolic member comprising a sleeve which is coupled to the embolic structure and wherein a distal end of the sleeve is disposed proximal to a distal end of the embolic structure; and
   restricting blood flow through the embolic member.

16. The method of claim 15, further comprising releasing the embolic structure from a delivery wire by rotating the delivery wire relative to the embolic structure.

17. The method of claim 15, further comprising re-capturing the embolization device to reposition the embolization device within the vessel or to remove the intravascular occlusion device from the vessel.

* * * * *